US006197769B1

(12) United States Patent
Alisi et al.

(10) Patent No.: US 6,197,769 B1
(45) Date of Patent: Mar. 6, 2001

(54) INDAZOLE AMIDE COMPOUNDS AS SEROTONINERGIC AGENTS

(75) Inventors: Alessandra Alisi, Rome; Mario Brufani, Castel Gandolfo; Nicola Cazzolla, Ariccia; Marilena Giannangeli, Rome; Mario Pinza, Corsico, all of (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 09/403,007

(22) PCT Filed: Apr. 2, 1998

(86) PCT No.: PCT/EP98/02129

§ 371 Date: Nov. 22, 1999

§ 102(e) Date: Nov. 22, 1999

(87) PCT Pub. No.: WO93/03725

PCT Pub. Date: Mar. 4, 1993

(30) Foreign Application Priority Data

Apr. 15, 1997 (IT) .............................. MI97A0867

(51) Int. Cl.[7] ................. A61P 13/10; C07D 413/14; A61K 31/5377

(52) U.S. Cl. ............. 514/234.5; 514/241; 514/242; 514/63; 514/252.03; 514/256; 514/322; 544/107; 544/180; 544/182; 544/238; 544/364; 544/333; 544/215; 544/129; 544/130; 546/199; 546/184

(58) Field of Search ................... 544/107, 180, 544/182, 238, 364, 333, 215, 129, 130; 546/199; 514/63, 241, 242, 234.5, 252.03, 253.09, 256, 322

(56) References Cited

FOREIGN PATENT DOCUMENTS

0732333 * 5/1996 (EP) .
0829474 * 5/1996 (EP) .
9303725 * 3/1993 (WO) .
9846589 * 10/1998 (WO) .

* cited by examiner

*Primary Examiner*—Robert W. Ramsuer
*Assistant Examiner*—Sonya Wright
(74) *Attorney, Agent, or Firm*—Oblon, Spivak, McClelland, Maier & Neustadt, P.C.

(57) ABSTRACT

A compound having general formula (I) wherein $R_1$, $R_2$, $R'_3$, $R_4$, and $R_6$ have the meanings stated in the description, acid addition salts thereof with pharmaceutically acceptable organic and inorganic acids an pharmaceutically acceptable quaternary salts thereof.

18 Claims, No Drawings

INDAZOLE AMIDE COMPOUNDS AS SEROTONINERGIC AGENTS

The present invention relates to an indazole amide compound possessing a serotoninergic action, a method for preparing thereof and the pharmaceutical compositions containing the same.

Amongst the numerous known families of serotonin receptors, the 5HT$_4$ receptors have only recently been identified in the urinary bladder, smooth and cardiac muscle and specific areas of the central nervous system. Compounds possessing agonistic, partially agonistic and antagonistic actions against such receptors are of potential interest in pharmacological treatment of disorders of gastrointestinal motility, disorders of the central nervous system, urinary incontinence and cardiac arrhythmia. The action of such compounds in fact takes place by mimicking or antagonising the ability of serotonin to stimulate intestinal motility by activation of the enteric neurons, to modulate important cerebral processes such as training, memory and anxiety, to induce relaxation of the urinary bladder and to increase frequency of atrial contraction.

A family of indazole amide compounds has now been found which possess affinity with 5HT$_4$ receptors and which act as antagonists of serotonin.

It is therefore a first object of the present invention to provide an indazole amide compound having the general formula:

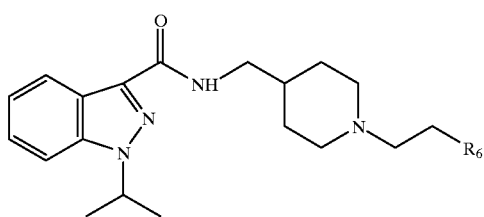

(I)

wherein

R$_6$ is selected from the group comprising, C$_{3-7}$ cycloalkyl, heterocyclic ring having from 5 to 6 members where 1 to 4 members are heteroatoms, the same or different from each other, selected from the group comprising N, O and S, dimethylamino C$_{1-3}$ alkyl, methoxy C$_{1-3}$ alkyl, N-phenyl amide, aminosulphonylmethyl, dihydroxy C$_{2-3}$ alkyl, aryl substituted by hydroxy; acid addition salts thereof with pharmaceutically acceptable organic and inorganic acids and pharmaceutically acceptable quaternary salts thereof.

Preferred examples of aryl are phenyl, naphthyl and biphenyl.

Preferred examples of heterocyclic rings are thienyl, furanyl, pyranyl, pyrrolyl, imidazolyl, pyrazolyl, isoxazolyl, pyridinyl, pyrazinyl, pyrimidinyl, pyridazinyl, furazanyl, pyrroilnyl, imidazolinyl, pyrazolidinyl, pyrazolinyl, piperidinyl, piperazinyl, morpholinyl, triazinyl, thiazolyl, tetrazolyl and thiadiazolyl. Typical examples of R$_6$ are cyclopropyl, cyclohexyl, pyridinyl, tetrazolyl, morpholinyl, methoxymethyl, methoxypropyl, hydroxyphenyl, dimethylaminomethyl and aminosulphonylmethyl.

It is a second object of the present invention to provide a process for preparing a compound of the formula (I), acid addition salts thereof with pharmaceutically acceptable organic and inorganic acids and pharmaceutically acceptable quaternary salts thereof, comprising:

a) acylating a 4-aminomethyl piperidine of the formula:

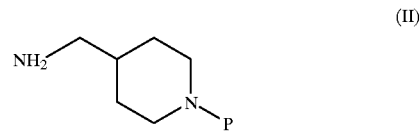

(II)

wherein

P is a suitable protecting group;

by means of a 1-alkyl-indazole-3-carboxylic acid halide of the formula:

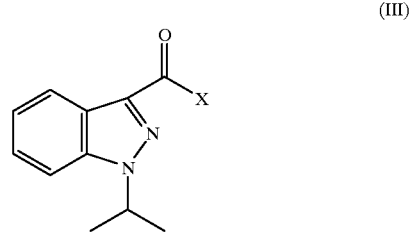

(III)

wherein

X is halogen, to give a compound of the formula:

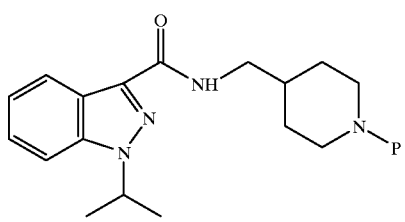

(IV)

b) de-protecting a compound of the formula (IV) to give a compound of the formula:

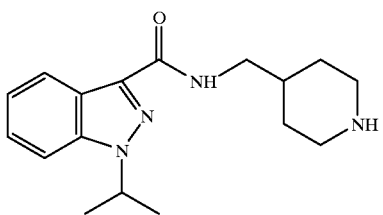

(V)

c) alkylating a compound of the formula (V) with a compound of the formula (VI) to give a compound of the formula (I) according to the following reaction scheme:

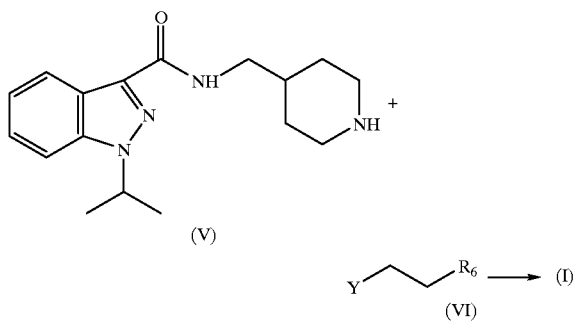

(V)

$$Y\diagup\diagdown R_6 \longrightarrow (I)$$

(VI)

wherein

R$_6$ has the above mentioned meanings, and

Y is halogen, d) optionally forming an acid addition salt of an indazole amide compound of the formula (I) with a pharmaceutically acceptable organic or inorganic acid, or a pharmaceutically acceptable quaternary salt of an indazole amide compound of the formula (1).

Typical examples of protecting groups (P) are benzyloxycarbonyl, benzyl, terbutoxycarbonyl and trimethylsilylethoxycarbonyl.

Step a) is preferably carried out by reacting a compound of the formula (II) with a compound of the formula (III) in which X is chlorine, in the presence of a suitable diluent and at a temperature of from 0 to 140° C. for a period of time of from 0.5 to 20 hours.

Preferably the diluent is aprotic, polar or apolar. Still more preferably, it is aprotic apolar. Examples of suitable aprotic apolar diluents are aromatic hydrocarbons such as, for example, benzene, toluene and xylenes. Examples of suitable aprotic polar diluents are dimethylformamide and dimethylsulphoxide.

Still more preferably, the reaction is performed at a temperature of from 15 to 40° C. for a period of time of from 1 to 14 hours.

In turn, step (b) is carried out according to techniques known to the person skilled in the art of the protecting group (Theodora W. Greene and Peter G. M. Wuts, "Protective groups in organic synthesis", pp. 309–406, John Wiley & Sons, Inc., N.Y., 1991). In the case of benzyl and benzyloxycarbonyl, the deprotection of the protecting group is preferably carried out by catalytic hydrogenation. An example of a suitable catalyst is palladium on activated carbon.

Preferably the deprotection is carried out by hydrogenation in the presence of a suitable diluent such as, for example, a low aliphatic alcohol, a low aliphatic acid and mixtures thereof. An example of a preferred diluent is an ethyl alcohol/acetic acid mixture.

Step c) is preferably performed with a compound of the formula (VI), in which Y is chlorine or bromine in the presence of a suitable acceptor of acids such as, for example, alkali carbonates and bicarbonates, low trialkylamines and a suitable diluent such as, for example, aromatic hydrocarbons, dimethylformamide and aliphatic low alcohols.

Typical examples of preferred organic and inorganic acids for forming addition salts of the present invention (step d) are oxalic, maleic, tartaric, methanesulphonic, sulphuric, phosphoric acid, hydrogen bromide and hydrogen chloride.

Methyl iodide is a typical example of a preferred compound forming a pharmaceutically acceptable quaternary salt of the invention.

The preparation of the above mentioned salts comprises addition (step d) of a pharmaceutically acceptable organic or inorganic acid, or of methyl iodide to an indazole amide compound of the formula (I) obtained in step c).

The intermediates of formula (IV) and (V) are new. They are therefore a further object of the present invention.

Alternatively, indazole amide compound of the formula (I) can be prepared by acylation of a suitable 4-aminomethyl piperidine with a compound of the formula (III).

Typical examples of pathological conditions which might benefit from treatment with a pharmaceutical composition according to this invention are all the pathologies which are responsive to treatment with antagonists of 5-HT$_4$ receptor such as, for example, gastrointestinal disorders associated with high intestinal motility, such as IBS (irritable bowel syndrome), urinary incontinence, and cardiac arrhythmias such as atrial fibrillation.

Preferably, the pharmaceutical compositions of the present invention will be prepared in suitable dosage forms comprising an effective dose of at least one compound of the formula (I) or a pharmaceutically acceptable addition salt thereof or a quaternary salt thereof and at least one pharmaceutically acceptable inert ingredient.

Examples of suitable dosage forms are tablets, capsules, coated tablets, granules, solutions and syrups for oral administration; creams, ointments and medicated adhesive strips for topical administration; suppositories for rectal administration and sterile solutions for injectable, aerosol or ophthalmic administration.

The dosage forms may also contain other conventional ingredients such as stabilizing agents, preservatives, surfactants, buffers, salts for adjusting the osmotic pressure, emulsifiers, sweeteners, coloring agents, flavoring agents, and the like.

When required by particular therapies, the pharmaceutical composition of the present invention may contain other pharmacologically active ingredients whose concomitant administration is therapeutically useful.

The amount of the compound of formula (I) or of a pharmaceutically acceptable salt thereof may vary within a wide range depending on known factors such as, for example, the type of disease to be treated, the severity of the disease, the patient's body weight, the dosage form, the chosen route of administration, the number of dosage forms administered per day and the effectiveness of the chosen compound of formula (I). However, the optimum amount may be easily and routinely determined by a person skilled in the art.

Typically, the amount of the compound of formula (I) or of a salt thereof in the pharmaceutical composition of this invention will be such as to insure an administered dosage level of from 0.001 to 50 mg/kg/day.

The dosage forms of the pharmaceutical composition according to this invention may be prepared according to methods which are known to the pharmaceutical chemist and comprise mixing, granulation, compression, dissolution, sterilization, and the like.

The following Examples are intended to illustrate the present invention, without limiting it in any way.

EXAMPLE 1

Preparation of 1-isopropyl-1H-3-indazolecarbonyl chloride (III: R$_1$=H, R$_2$=C$_3$H$_7$)

a) 2-methylpropyl-1-isopropyl-1H-3-indazolecarboxylate

To a solution of 2-methylpropyl-1H-3-indazolecarboxylate (50 g; 0.24 moles) in 1,2-dimethoxyethane (300 ml) a solution of isopropyl bromide (27.5 ml; 0.29 moles) in 1,2-dimethoxy-ethane (100 ml) and KOH (13.5 g; 0.24 moles) was added and the mixture was heated under reflux for 8 hours. After removal of the solvent, the residue was dissolved in toluene (300 ml), the thus obtained solution was washed with 1N NaOH (100 ml), $H_2O$ (2×100 ml) and then dried and concentrated in vacuum. The residue was purified from the isomer 2-methylpropyl-2-isopropyl-2H-3-indazolecarboxylate via flash chromatography (eluent, hexane:ethyl acetate=95:5) to give the title compound (23 g) as an oil.

$^1$H NMR (CDCl$_3$, δ): 1.07 (d, J=7 Hz, 6H); 1.66 (d, J=7 Hz, 6H); 1.95–2.48 (m, 1H); 4.26 (d, J=7 Hz, 2H); 4.96 (hept. J=7 Hz, 1H); 7.15–7.70 (m, 3H); 8.03–8.33 (m, 1H).

b) 1-isopropyl-1H-3-indazolecarboxylic acid

A suspension of the compound of the Example 1a) (10 g; 0.04 moles) in 0.75N NaOH (100 ml) was heated under reflux for 12 hours. The solution was then cooled, acidified with 6N HCl (40 ml), the solid precipitate was filtered and recrystallized from 1:1 hexane/ethyl acetate to give the title compound (5.5 g), m.p. 162–3° C. (Harada H. et al., "Chem. Pharm. Bull.", 43(11), 1912–1930, 1995).

$^1$H NMR (DMSO, δ); 1.54 (d, J=7 Hz, 6H); 5.13 (hept, J=7 Hz, 1H); 7.20–7.65 (m, 2H); 7.85 (d, J=8 Hz, 1H); 8.14 (d, J=7 Hz, 1H); 13.08 (s broad, 1H).

c) 1-isopropyl-1H-3-indazolecarbonyl chloride

Thionyl chloride (4 ml, 0.054 moles) was added to a stirred solution of the compound of the Example 1b) and the mixture was stirred under reflux for 2 hours. After removal of the solvent in vacuum, the residue was recrystallized from hexane to give 3.5 g of the title compound, m.p. 63–4° C.

| Elemental analysis for $C_{11}H_{11}ClN_2O$ | C | H | N |
|---|---|---|---|
| % found: | 59.29 | 5.20 | 12.76 |
| % calculated: | 59.33 | 4.98 | 12.58 |

$^1$H NMR (CDCl$_3$, δ); 1.69 (d, J=7 Hz, 6H); 5.00 (hept., J=7 Hz, 1H); 7.20–7.70 (m, 3H); 8.03–8.33 (m, 1H).

EXAMPLE 2

Preparation of N3-{[1-(2-phenylethyl)-4-piperidinyl]methyl}-1-isopropyl-1H-3-indazolecarboxamide hydrochloride (AFR 306)

(I: $R_1=R_3=R'_3=R_4=R_5$=H, $R_2=C_3H_7$, $R_6=C_6H_5$)

[1-(2-phenylethyl)-1-piperidinyl]methylamine (3 g; 0.014 moles), prepared as described in EP-A-0 343 307, in toluene (30 ml) was dropped into a suspension of the compound of the Example 1c) (3 g, 0.014 moles) in toluene (30 ml). After 3 hours at room temperature, the solid was filtered, dissolved in $H_2O$ made basic with 6N NaOH solution and extracted with $CH_2Cl_2$ (2×200 ml). The solvent was removed by evaporation, the residue was purified on $SiO_2$ column (eluent, CHCl$_3$: MeOH=95:5) and transformed into the corresponding hydrochloride. The obtained product (2 g) melted at 211–212° C.

| Elemental analysis for $C_{25}H_{33}ClN_4O$ | C | H | N | Cl$^-$ |
|---|---|---|---|---|
| % found: | 68.13 | 7.52 | 12.78 | 8.03 |
| % calculated: | 68.09 | 7.54 | 12.70 | 8.04 |

$^1$H NMR (DMSO, δ); 1.56 (d, J=7 Hz, 6H); 1.50–2.30 (m, 5H); 2.70–3.90 (m, 10H); 5.10 (hept, J=7 Hz, 1H); 7.05–7.63 (m, 7H); 7.81 (d, J=8 Hz, 1H); 8.21 (d, J=8 Hz, 1H); 8.47 (t, J=6 Hz, 1H); 11.05 (s broad, 1H).

IR (KBr): $v_{co}$ 1652 cm$^{-1}$.

EXAMPLE 3

Preparation of N3-{[1-(phenylmethyl)-4-piperidinyl]methyl}-1-isopropyl-1H-3-indazolecarboxamide (IV: $R_1=R_3=R'_3=R_4=R_5$=H, $R_2=C_3H_7$, P=—CH$_2$C$_6$H$_5$)

To a stirred solution of 1-isopropyl-1H-3-indazolecarbonyl chloride (52 g; 0.234 moles) in toluene (300 ml) it was added dropwise a solution of [1-(phenylmethyl)-4-piperidinyl]methylamine, prepared as described in WO 94/10174, (47.7 g; 0.234 moles) in toluene (200 ml). After 5 hours, the solvent was removed by evaporation under reduced pressure. The reaction mixture was treated with 2N NaOH, extracted with dichloromethane and concentrated in vacuum. The solid residue (95 g) was recrystallized from 7:3 hexane/ethyl acetate to afford the title compound as a white solid (45 g), m.p. 72–74° C.

| Elemental analysis for $C_{24}H_{30}N_4O$ | C | H | N |
|---|---|---|---|
| % found: | 73.78 | 7.87 | 14.35 |
| % calculated: | 73.81 | 7.74 | 14.35 |

$^1$H NMR (CDCl$_3$, δ); 1.59 (d, J=7 Hz, 6H); 1.10–2.25 (m, 7H); 2.80–3.15 (m, 2H); 3.27–3.60 (m, 4H); 4.86 (hept, J=7 Hz, 1H); 7.00–7.60(m, 9H); 8.27–8.52(m, 1H).

IR (KBr): $v_{co}$ 1641 cm$^{-1}$.

EXAMPLE 4

Preparation of N3-(4-piperidinylmethyl)-1-isopropyl-1H-3-indazolecarboxamide hydrochloride (V: $R_1=R_3=R'_3=R_4=R_5$=H, $R_2=C_3H_7$)

A suspension of the product of the Example 3 (28 g; 0.076 moles) in ethyl alcohol (1500 ml) and glacial acetic acid (66 ml) was hydrogenated over 10% Pd—C (13.4 g) at 35 psi for 24 hours. The mixture was filtered and the filtrate concentrated in vacuum. The residue was dissolved in water, treated with 5N NaOH and stirred for 2 hours at room temperature. The solid obtained was filtered off (16.6 g) and converted to the corresponding hydrochloride (9.5 g), m.p. 211–214° C. (dec.)

| Elemental analysis for $C_{17}H_{25}ClN_4O \cdot \frac{1}{2}H_2O$ | C | H | N |
|---|---|---|---|
| % found: | 58.82 | 7.68 | 16.36 |
| % calculated: | 59.03 | 7.58 | 16.20 |

$^1$H NMR (DMSO, δ); 1.55 (d, J=7 Hz, 6H); 1.31–2.18 (m, 5H); 2.58–3.64 (m, 7H); 5.09 (hept, J=7 Hz, 1H); 7.12–7.60 (m, 2H); 7.80 (d, J=8 Hz, 1H); 8.20 (d, J=8 Hz, 1H); 8.41 (t, J=6 Hz, 1H); 8.82–9.60 (m, 2H).

IR (KBr): $v_{co}$ 1658 cm$^{-1}$.

EXAMPLE 5

Preparation of N3-{[1-(4-phenylbutyl)-4-piperidinyl]methyl}-1-isopropyl-1H-3-indazolecarboxamide oxalate (AFR603)

(I: $R_1=R_3=R'_3=R_4=R_5=H$, $R_2=C_3H_7$, $R_6=$—CH$_2$CH$_2$C$_6$H$_5$)

To a stirred suspension of the product of Example 4 as free base (5.27 g; 15.6 mmoles) in ethyl alcohol (20 ml), K$_2$CO$_3$ (6.5 g: 50 mmoles) and 4-phenylbromobutane ("Braun", B-44, 2872, 1911) (3,6 g, 17.1 mmoles) were added. The reaction mixture was stirred at reflux for 10 hours. After removal of the solvent, the residue was partitioned between ethyl acetate and 1N HCl. The water phase was made basic with 2N NaOH, extracted with ethyl acetate and concentrated in vacuum. The solid was converted to the corresponding oxalate salt (2 g), m.p. 154–155° C.

| Elemental analysis for $C_{29}H_{38}N_4O_5 \cdot \frac{1}{2}H_2O$ | C | H | N |
|---|---|---|---|
| % found: | 65.87 | 7.47 | 10.62 |
| % calculated: | 65.52 | 7.39 | 10.54 |

$^1$H NMR (DMSO, δ); 1.55 (d, J=7 Hz, 6H); 1.31–2.18 (m, 5H); 2.30–3.64 (m, 14H); 5.08 (hept, J=7 Hz, 1H); 7.12–7.60 (m, 7H); 7.80 (d, J=8 Hz, 1H); 8.19 (d, J=8 Hz, 1H); 8.41 (t, J=6 Hz, 1H).

EXAMPLE 6

Preparation of N3-{[1-(2-cyclohexylethyl)-4-piperidinyl]methyl}-1-isopropyl-1H-3-indazolecarboxamide hydrochloride (AFR604)

(I: $R_1=R_3=R'_3=R_4=R_5=H$, $R_2=C_3H_7$, $R_6=C_6H_{11}$)

Following the procedure of Example 5, N3-(4-piperidinylmethyl)-1-isopropyl-1H-3-indazolecarboxamide (4.42 g) and (2-bromoethyl)-cyclohexane ("J.A.C.S.", 48, 1089–1093, 1926) (4.63 g) gave the title compound (2.5 g), m.p. 244–246° C. (dec.)

| Elemental analysis for $C_{25}H_{39}N_4O \cdot \frac{1}{2}H_2O$ | C | H | N | Cl$^-$ |
|---|---|---|---|---|
| % found: | 65.51 | 9.05 | 12.57 | 7.89 |
| % calculated: | 65.83 | 8.84 | 12.28 | 7.77 |

$^1$H NMR (DMSO, δ); 1.55 (d, J=7 Hz, 6H); 0.68–2.18 (m, 17H); 2.63–3.70 (m, 10H); 5.09 (hept, J=7 Hz, 1H); 7.12–7.60 (m, 2H); 7.80 (d, J=8 Hz, 1H); 8.20 (d, J=8 Hz, 1H); 8.41 (t, J=6 Hz, 1H); 10.70 (s broad 1H).

IR (KBr): $v_{co}$ 1656 cm$^{-1}$.

EXAMPLE 7

Preparation of N3-({1-[3-(dimethylamino)propyl]-4-piperidinyl}methyl)-1-isopropyl-1H-3-indazolecarboxamide dimaleate (AFR606)

(I: $R_1=R_3=R'_3=R_4=R_5=H$, $R_2=C_3H_7$, $R_6=$—CH$_2$NC$_2$H$_6$)

Following the procedure of Example 5, N3-(4-piperidinylmethyl)-1-isopropyl-1H-3-indazolecarboxamide (3 g) and N-(3-chloropropyl)-N,N-dimethylamine hydrochloride (580 mg) gave the title compound (950 mg), m.p. 155–156° C.

| Elemental analysis for $C_{30}H_{43}N_5O_9 \cdot \frac{1}{2}H_2O$ | C | H | N |
|---|---|---|---|
| % found: | 57.83 | 7.01 | 11.11 |
| % calculated: | 57.50 | 7.08 | 11.18 |

$^1$H NMR (DMSO, δ); 1.55 (d, J=7 Hz, 6H); 1.68–2.28 (m, 7H); 2.81 (s, 6H); 2.75–3.75 (m, 11H); 5.09 (hept, J=7 Hz, 1H); 6.09 (s, 4H); 7.12–7.60 (m, 2H); 7.81 (d, J=8 Hz, 1H); 8.20 (d, J=8 Hz, 1H); 8.45 (t, J=6 Hz, 1H).

EXAMPLE 8

Preparation of N3-({1-[2-(4-morpholinyl)ethyl]-4-piperidinyl}methyl)-1-isopropyl-1H-3-indazolecarboxamide dihydrochloride (AFR607)

(I: $R_1=R_3=R'_3=R_4=R_5=H$, $R_2=C_3H_7$, $R_6=C_4H_4NO$)

Following the procedure of Example 5, N3-(4-piperidinylmethyl)-1-isopropyl-1H-3-indazolecarboxamide (3 g) and 4-(2-chloroethyl)-morpholine (3.42 g) gave the title compound (3.2 g), m.p. 266–267° C. (dec.)

| Elemental analysis for $C_{23}H_{37}Cl_2N_5O_2 \cdot \frac{1}{2}H_2O$ | C | H | N | Cl$^-$ |
|---|---|---|---|---|
| % found: | 55.74 | 7.61 | 13.96 | 14.12 |
| % calculated: | 55.75 | 7.73 | 14.13 | 14.31 |

$^1$H NMR (DMSO, δ); 1.55 (d, J=7 Hz, 6H); 1.30–2.25 (m, 5H); 2.75–4.30 (m, 19H); 5.09 (hept, J=7 Hz, 1H); 7.12–7.60 (m, 2H); 7.81 (d, J=8 Hz, 1H); 8.20 (d, J=8 Hz, 1H); 8.45 (t, J=6 Hz, 1H); 10.80 (s broad, 1H); 10.60 (s broad, 1H).

IR (KBr): $v_{co}$ 1652 cm$^{-1}$.

EXAMPLE 9

Preparation of N3-[(1-{2-[(methylsulphonyl)amino]ethyl}4-piperidinyl)methyl]-1-isopropyl-1H-3-indazolecarboxamide hydrochloride (AFR703)

(I: $R_1=R_3=R'_3=R_4=R_5=H$, $R_2=C_3H_7$, $R_6=CH_3SO_2NH-$)

Following the procedure of Example 5, N3-(4-piperidinylmethyl)-1-isopropyl-1H-3-indazolecarboxamide (5 g) N-(2-bromoethyl)-methane sulphonamide (WO 93/18036) (3 g) gave the title compound (1.5 g), m.p. 186–187° C. (dec.)

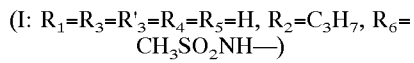

| Elemental analysis for $C_{20}H_{32}ClN_5O_3S$ | C | H | N | S | Cl⁻ |
|---|---|---|---|---|---|
| % found: | 52.15 | 7.22 | 15.30 | 6.98 | 7.77 |
| % calculated: | 52.45 | 7.04 | 15.29 | 7.00 | 7.74 |

$^1$H NMR (DMSO, δ); 1.55 (d, J=7 Hz, 6H); 1.40–2.30 (m, 5H); 3.00 (s, 3H); 2.75–3.80 (m, 10H); 5.09 (hept, J=7 Hz, 1H); 7.12–7.70 (m, 3H); 7.80 (d, J=8 Hz, 1H); 8.20 (d, J=8 Hz, 1H); 8.45 (t, J=6 Hz, 1H); 10.73 (s broad, 1H).

IR (KBr): $v_{co}$ 1651 cm$^{-1}$.

EXAMPLE 10

Preparation of N3-({1-[2-(2-pyridinyl)ethyl]4-piperidinyl}methyl)-1-isopropyl-1H-3-indazolecarboxamide hydrochloride (AFR605)

(I: $R_1=R_3=R'_3=R_4=R_5=H$, $R_2=C_3H_7$, $R_6=C_5H_4N$)

To a stirred suspension of the product of Example 4 as free base (10 g; 33.3 mmoles), 2-vinylpyridine (3.6 g; 34 mmoles), glacial acetic acid (2 ml) and water (2.5 ml) were added. After 16 hours at 95° C., the reaction mixture was made basic with 2N NaOH, extracted with ethyl acetate and concentrated in vacuum. The residue was purified by flash silica-gel chromatography with CHCl$_3$:MeOH=97:3 as eluent to yield a solid which was converted to hydrochloride salt (5 g), m.p. 122–123° C. (dec.)

| Elemental analysis for $C_{24}H_{32}ClN_5O.H_2O$ | C | H | N | Cl⁻ |
|---|---|---|---|---|
| % found: | 62.80 | 7.42 | 15.18 | 7.78 |
| % calculated: | 62.66 | 7.45 | 15.22 | 7.71 |

$^1$H NMR (DMSO, δ); 1.55 (d, J=7 Hz, 6H); 1.68–2.30 (m, 5H); 2.80–3.78 (m, 12H); 5.10 (hept, J=7 Hz, 1H); 7.12–7.60 (m, 4H); 7.68–8.00 (m, 2H); 8.21 (d, J=7 Hz, 1H); 8.33–8.70 (m, 2H); 11.05 (s broad, 1H).

IR (KBr): $v_{co}$ 1644 cm$^{-1}$.

Test 1

Antagonistic Action on 5-HT$_4$ Receptor

The antagonistic action of the compounds of the formula (I) was evaluated by testing the influence of the compound under evaluation on serotonin-induced relaxation of rat oesophageal tunica pre-contracted with carbachol according to the method described by J. D. Gale et al. in "Br. J. Pharmacol.", 111, 332–338, (1994).

All the tested compounds of the invention showed a pA$_2$>8. The specific values for AFR 603, AFR 604, AFR 605 and AFR 306 are shown Table 1 below

TABLE 1

| Compound | pA$_2$ | s.e. |
|---|---|---|
| AFR 603 | 9.12 | 1.42 |
| AFR 604 | 8.19 | 0.99 |
| AFR 605 | 10.8 | 1.90 |
| AFR 306 | 9.36 | 0.38 | s.e. = standard error

What is claimed is:

1. A compound having the general formula

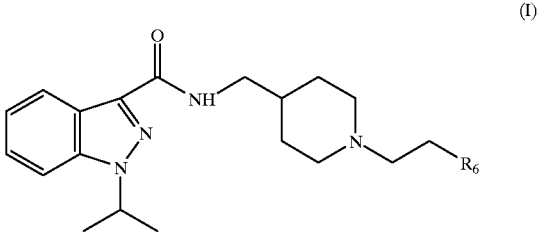

(I)

wherein

R$_6$ is selected from the group consisting of, C$_{3-7}$ cycloalkyl, heterocyclic ring having from 5 to 6 members where 1 to 4 members are heteroatoms, the same or different from each other, selected from the group consisting of N, O and S, dimethylamino C$_{1-3}$ alkyl, methoxy C$_{1-3}$ alkyl, N-phenyl amide, aminosulphonylmethyl, dihydroxy C$_{2-3}$ alkyl, and aryl substituted by hydroxy;

acid addition salts thereof with pharmaceutically acceptable organic and inorganic acids and pharmaceutically acceptable quaternary salts thereof.

2. The compound according to claim 1, wherein the heterocyclic ring is selected from the group consisting of thienyl, furanyl, pyranyl, pyrrolyl, imidazolyl, pyrazolyl, isoxazolyl, pyridinyl, pyrazinyl, pyrimidinyl, pyridazinyl, furazanyl, pyrrolinyl, imidazolinyl, pyrazolidinyl, pyrazolinyl, piperidinyl, piperazinyl, morpholinyl, triazinyl, thiazolyl, tetrazolyl and thiadiazolyl.

3. The compound according to claim 1, wherein R$_6$ is selected from the group consisting of cyclopropyl, cyciohexyl, pyridinyl, tetrazolyl, morpholinyl, methoxymethyl, methexypropyl, hydroxyphenyl, dimethylaminomethyl and aminosulphonylmethyl.

4. The compound according to claim 1, wherein R$_6$ is cyclohexyl.

5. The compound according to claim 1, wherein R$_6$ is pyridinyl.

6. The compound according to claim 1, wherein R$_6$ is dimethylaminomethyl.

7. The compound according to claim 1, wherein R$_6$ is morpholinyl.

8. The compound according to claim 1, wherein R$_6$ is aminosulphonylmethyl.

9. A process for preparing a compound of the formula (I), acid addition salts thereof with pharmaceutically acceptable organic and inorganic acids and pharmaceutically acceptable quaternary salts thereof, comprising:

a) acylating a 4-aminomethyl piperidine of the formula:

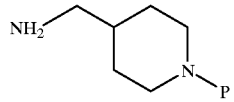
(II)

wherein

P is a suitable protecting group by means of a 1-alkyl-indazole-3-carboxylic acid halide of the formula:

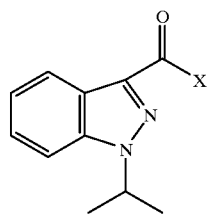
(III)

wherein

X is halogen, to give a compound of the formula:

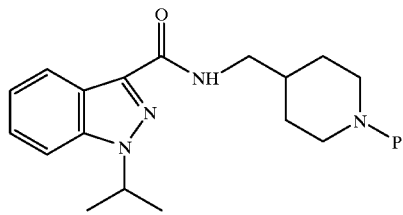
(IV)

b) de-protecting a compound of the formula (IV) to give a compound of the formula:

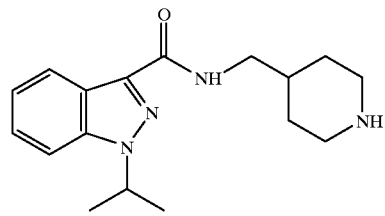
(V)

c) alkylating a compound of the formula (V) with a compound of the formula (VI) to give a compound of the formula (I) according to the following reaction scheme:

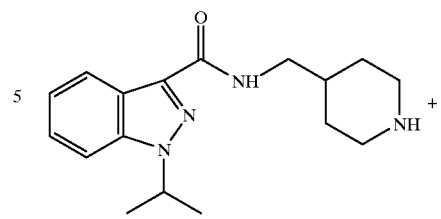
(V)

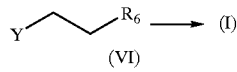
(VI) → (I)

wherein $R_6$ is selected from the group consisting of, $C_{3-7}$ cycloalkyl, heterocyclic ring having from 5 to 6 members where 1 to 4 members are heteroatoms, the same or different from each other, selected from the group consisting of N, O and S, dimethylamino $C_{1-3}$ alkyl methoxy $C_{1-3}$ alkyl, N-phenyl amide, aminosulphonylmethyl, dihydroxy $C_{2-3}$ alkyl, and aryl substituted by hydroxy, and Y is halogen, d) optionally forming an acid addition salt of an indazole amide compound of the formula (I) with a pharmaceutically acceptable organic or inorganic acid, or a pharmaceutically acceptable quaternary salt of an indazole amide compound of the formula (I).

10. The process according to claim 9, wherein P is selected from the group comprising benzyloxycarbonyl, benzyl, terbutoxycarbonyl, and trimethylsilylethoxycarbonyl.

11. The process according to claim 9, wherein step a) is carried out by reacting a compound of the formula (II) with a compound of the formula (III) in which X is chlorine, in the presence of a diluent and at a temperature of from 0 to 140° C. for a period of time of from 0.5 to 20 hours.

12. The process according to claim 10, wherein when P is benzyl or benzyloxycarbonyl, step b) is carried out by catalytic hydrogenation.

13. The process according to claim 9 wherein when in a compound of the formula (VI), Y is chlorine or bromine, step c) is performed in the presence of an acceptor of acids and in the presence of a diluent.

14. The process according to claim 9, wherein methyliodide forms a pharmaceutically acceptable quaternary salt of a compound of formula (I), step (d).

15. An intermediate compound having the general formula:

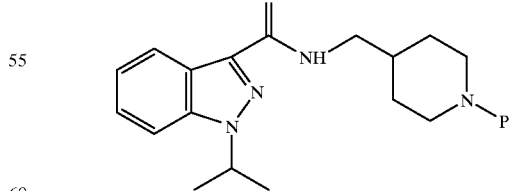
(IV)

wherein

P is selected from the group consisting of benzyloxycarbonyl, terbutoxycarbonyl and trimethylsilylethoxycarbonyl.

16. A pharmaceutical composition, wherein said composition comprises an effective dose of at least one compound of the formula:

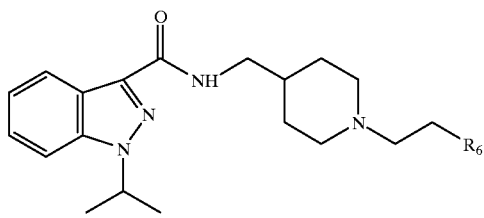

(I)

wherein $R_6$ is selected from the group consisting of $C_{3-7}$ cycloalkyl, heterocyclic ring having from 5 to 6 members where 1 to 3 members are heteroatoms, the same or different from each other, selected from the group consisting of N, O and S, dimethylamino $C_{1-3}$ alkyl, methoxy $C_{1-3}$ alkyl, N-phenyl amide, aminosulphonylmethyl, dihydroxy $C_{2-3}$ alkyl, aryl, and aryl substituted by hydroxy;

acid addition salts thereof with pharmaceutically acceptable organic and inorganic acids and pharmaceutically acceptable quaternary salts thereof.

17. A method of antagonizing 5-$HT_4$ receptors, comprising contacting 5-$HT_4$ receptors with the compound of claim 1.

18. A method of treating pathological conditions which are responsive to 5-$HT_4$ receptor antagonists, comprising administering an effective amount of the compound of claim 1 to a patient in need thereof.

* * * * *

UNITED STATES PATENT AND TRADEMARK OFFICE
CERTIFICATE OF CORRECTION

| | |
|---|---|
| PATENT NO. : 6,197,769 B1 | |
| DATED : March 6, 2001 | |
| INVENTOR(S) : Alisi et al. | |

It is certified that error appears in the above-identified patent and that said Letters Patent is hereby corrected as shown below:

<u>Title page,</u>
Item [87], the PCT Pub. No. and the PCT Pub. Date are incorrect. Item [87] should read as follows:

[87]    PCT Pub. No.: WO98/46589
        PCT Pub. Date: Oct. 22, 1998

Signed and Sealed this

Twentieth Day of November, 2001

Attest:

*Nicholas P. Godici*

NICHOLAS P. GODICI
*Attesting Officer*    *Acting Director of the United States Patent and Trademark Office*